United States Patent [19]

Beitz et al.

[11] Patent Number: 5,292,639
[45] Date of Patent: Mar. 8, 1994

[54] ASSOCIATION OF BOVINE MITOCHONDRIAL DNA WITH TRAITS OF ECONOMIC IMPORTANCE

[75] Inventors: Donald C. Beitz; Albert E. Freeman, both of Ames, Iowa; Michael M. Schutz, Laurel, Md.; Gary L. Lindberg, Ames, Iowa

[73] Assignee: Iowa State University Research Foundation, Inc., Ames, Iowa

[21] Appl. No.: 872,265

[22] Filed: Apr. 24, 1992

Related U.S. Application Data

[63] Continuation-in-part of Ser. No. 398,898, Aug. 28, 1989.

[51] Int. Cl.$^5$ .................... C12Q 1/08; C12P 19/34; C07H 5/04; C07H 17/00
[52] U.S. Cl. .................................. 435/6; 536/18.7; 536/23.1; 536/24.3; 536/25.4; 935/78
[58] Field of Search .................... 435/6, 172.3, 91; 436/501, 614; 536/27, 18.7, 23.1, 24.3, 25.4; 935/3, 9, 63, 78

[56] References Cited

PUBLICATIONS

Laipis, et al. "Unequal Partitioning of Bovine Mitochondrial Genotypes Among Siblings" *Proc. Natl. Acad. Sci. U.S.A.*, vol. 85 pp. 8107-8110, Nov. 1988.
Anderson, et al. "Complete Sequence of Bovine Mitochondrial DNA", *J. Mol. Biol.* 156, 683-717 (1982).
Ashley, et al. "Rapid Segregation of Heteroplasmic Bovine Mitochondria" *Nucleic Acids Research*, vol. 17, No. 18, pp. 7325-7331 (1989).
Hauswirth, et al. "Heterogeneous Mitochondrial DNA D-Loop Sequences in Bovine Tissue" *Cell*, vol. 37, 1001-1007 (1984).
Laipis, et al. "A Physical Map of Bovine Mitochondrial DNA From a Single Animal" *Biochimica et Biophysica Acta*, 565 (1979) 22-32.
King, et al. "Mapping of Control Elements in the Displacement Loop Region of Bovine Mitochondrial DNA" *The Journal of Biological Chemistry*, vol. 262, No. 13, pp. 6204-6213 (1987).
King et al., "Mitochondrial DNA Displacement Loop Structure Depends on Growth State in Bovine Cells" *The Journal of Biological Chemistry* vol. 262, No. 13, pp. 6214-6220 (1987).
Sanger, et al. "DNA Sequencing With Chain-Terminating Inhibitors" *Proc. Natl. Acad. Sci USA*, vol. 74, No. 12, pp. 5463-5467 (1977).
Anderson et al. J. Mol. Biol. 156:683 (1982).
Lapiz et al. Biochem. Bioph. Act. 565:20 (1979).
Lapiz et al. P.N.A.S. 85:8107 (1988).
King et al. J. of Biol. Chem.: 262 (13) 6214 (1987).
King et al. J. of Biol. Chem. 262(13): 6204 (1987).
Ashley et al. Nucleic Acids Res. 17(18):7325 (1989).

*Primary Examiner*—Christopher S. F. Low
*Assistant Examiner*—Miguel Escallon
*Attorney, Agent, or Firm*—Zarley, McKee, Thomte, Voorhees & Sease

[57] ABSTRACT

A method of genetically evaluating animals by using mitochondrial DNA is disclosed. Polymorphisms in mitochondrial DNA are detected by isolating, fragmenting, and sequencing the DNA. The restriction patterns and nucleotide sequences of mitochondrial DNA of different animals are correlated to expressed traits in the animals. This may be confirmed by comparing results to expression of the trait in maternal lineages of animals. Further, effects of maternal lineages are determined by partitioning maternal genetic variation from nuclear variation.

16 Claims, No Drawings

ASSOCIATION OF BOVINE MITOCHONDRIAL DNA WITH TRAITS OF ECONOMIC IMPORTANCE

CROSS REFERENCE TO A RELATED APPLICATION

This application is a continuation-in-part of an earlier filed, commonly assigned application, Beitz et al, Ser. No. 07/398,898, filed Aug. 28, 1989 and entitled, METHOD OF GENETIC EVALUATION OF ANIMALS BY USING MITOCHONDRIAL DNA.

BACKGROUND OF THE INVENTION

In genetically evaluating animals, researchers use theory based on nuclear genes. Higher organisms have a nucleus within their cells that contains nuclear genetic material. This has been the source of genetic material for scientists in analyzing genetic background and inheritance of animals. However, there are other organelles within the cells that have their own genetic makeup, one of which includes the mitochondria with its own DNA.

Until now, it was widely held that essentially no variation existed in mitochondrial DNA. This invention relates to the finding that there is variation, or polymorphism, within mitochondrial DNA, and these polymorphisms may be used to evaluate inheritable traits of animals.

The use of mitochondrial DNA is a significant advancement in the science of animal breeding. Current genetic improvement programs are based solely on use of nuclear genes. Classical animal breeding methods have been developed first by using mass selection and then by progressing to evaluation of lineages, pedigrees, selection index, and best linear unbiased prediction methods. Progeny testing is the breeding method used most often in cattle. All methods are based on use of nuclear genetic material. Mitochondrial genes are inherited maternally. That is, they are transmitted from a female to both sexes of progeny; males do not transmit mitochondrial genes to their progeny. Thus, in a progeny test, bull mothers pass their maternal genetic material to their sons, but these sons do not transmit this genetic material to their daughters. Both nuclear and mitochondrial genetic material contributes to the production records of bull mothers, but, because only nuclear material is transmitted through their sons to his daughters, the bull mothers may be over- or under-evaluated, depending upon the bull mother's mitochondrial contribution. If the magnitude of the cytoplasmic or mitochondrial effect is known, the pedigree estimate of the bull mother's contribution can be adjusted appropriately.

Milk volume and percentage of milk fat and milk protein (two constituents of milk, along with lactose and minerals) are economically the most important traits of dairy cattle. Reproduction and health of cattle, however, merit attention as well, because the interval between successive calvings and health costs also determine profitability of dairy cows. Effects of cytoplasmic inheritance on reproductive measures have been shown for number of days open (days from calving to next conception), days from calving to first detected estrus, first service conception rate, and number of services.

It has now been found that there are polymorphisms in mitochondrial DNA and that a method of isolating and preparing specific fragments of the mitochondrial DNA has been developed so that fragments in the mitochondrial DNA may be associated with phenotypic expression as a particular trait in the animal. This discovery has been applied specifically to a herd of dairy cattle by associating the presence of particular nucleotide substitutions in the D-loop region of mitochondrial DNA (mtDNA) with increased volume productions of milk and with greater milkfat content. Other associations are also made for important economic traits such as days open and certain health traits such as mastitis and reproductive problems.

Mitochondrial lineage influences on health differences of cattle have not been examined. Much work associating human diseases to mitochondrial DNA sequence differences has been reported. Kearns-Sayres Syndrome (KSS) and Leber's hereditary optic neuropathy (LHON) are examples of such diseases. In fact, LHON has been shown to be correlated with a single guanine-adenine transition that converts an arginine to a histidine in NADH dehydrogenase subunit 4 gene of mtDNA. Such mtDNA nucleotide sequence substitutions may affect health and other production traits in cattle.

Molecular variation in bovine mtDNA has been demonstrated through RFLP analysis and comparison of nucleotide sequences. Displacement loop (D-loop) sequences of mtDNA from 36 distinct registered maternal lineages available for this study were previously compared Lindberg, G. L. 1989. Sequence heterogenity of bovine mitochondrial DNA. Ph.D Dissertation, Iowa State University, Lib. Ames. University Microfilm order No. DA-9014925. Ann Arbor, Mich. Fifty-one sequence differences were located, including 48 single base pair (bp) substitutions, one 9-bp deletion, and two variable length poly G-C runs. Where possible, D-loops from two or more animals of the same maternal lineage were sequenced to verify accuracy of mtDNA isolation and nucleotide sequencing and to confirm constancy of mtDNA within maternal lineages, supra.

The D-loop region of mtDNA does not code for any known gene products; hence, sequence polymorphisms there would not alter specific protein chain subunits. Promoters for transcription of both heavy and light strands of mtDNA as well as the origin of heavy strand replication, however, lie within the D-loop. Thus, sequence differences in the mtDNA D-loop may alter transcription or replication rates. Moreover, such D-loop polymorphisms may serve as markers of differences elsewhere on the mtDNA genome in coding regions of genes that are associated with phenotypic expression of traits.

The primary objects of the invention are, therefore, to evaluate animals genetically by using their mitochondrial DNA by phenotypic analyses of differences between maternal lineages.

Another object of the invention is to use polymorphism in mitochondrial DNA of animals to associate the absence or presence of single or several markers with traits of economic importance including health trait importance in animals.

A further object of the invention is to determine the sequence of nucleotides in mitochondrial DNA fragments and associate presence or absence of specific nucleotide sequences of fragments with traits of economic and health importance.

A still further object is to associate polymorphism in mitochondrial DNA with its expression in the maternal lineage of an animal.

A further object is to provide for improved genetic evaluation of animals by phenotypically determining the relative worth of maternal lineages for economic traits.

Another object of the invention is to predictably isolate efficient milk producers and lineages of milk producers from dairy herds by evaluation of polymorphism in mitochondrial DNA.

Other objects of the invention will become apparent in the following disclosure.

SUMMARY OF THE INVENTION

The invention relates to the use of cytoplasmic genetic material, specifically the mitochondrial DNA, to genetically evaluate an animal. The mitochondrial DNA of an animal is isolated, fragmented and sequenced, and polymorphism within the mitochondrial DNA is detected. This polymorphism is then correlated with the presence or absence of a desired trait. This relationship may be further confirmed by comparing the lineage of animals showing polymorphisms with lineages not showing the polymorphisms. Additionally, values of maternal lineages can be determined on a phenotypic basis to improve accuracy of bull mother selection and choice of females as donors for embryo transplants.

DETAILED DESCRIPTION OF THE INVENTION

Mitochondria are the source of cytoplasmic genetic information. Mitochondria carry multiple copies of a circular genome that is replicated and expressed within the organelle and is inherited maternally. It is the only genetic element known to be inherited cytoplasmically in mammals. Mitochondrial DNA in animals codes for 13 polypeptides that have been identified as components of the ATP synthesis system and codes for all of the transfer RNAs used in mitochondrial protein synthesis. The only non-coding portion of the genome is a region of approximately 900 base pairs that is referred to as the displacement loop or "D-loop". This D-loop is involved in the control of transcription and replication of mitochondrial DNA. Variation in mitochondrial DNA will affect the size of the mitochondrial DNA population in the cell, abundance of mitochondrial DNA gene transcripts and translation products, and mitochondrial oxidative energy transduction capacity.

As discussed more fully below, this invention involves the discovery that polymorphisms within the mitochondrial DNA of mammals can be associated with expressed traits in mammals.

Mitochondrial DNA is first obtained from the blood of the animal. A variety of methods exist for isolating mitochondrial DNA, such as Lindberg, G. L., Koehler, C. M., Mayfield, J. M., Myers, A. M., and Beitz, D. C. 1992 Biochem. Genet. 30:27, and incorporated herein by reference. One procedure is described in more detail in the example below.

After isolating the mitochondrial DNA, it then can be cloned, and typically this is done in *Escherichia coli* cells. This cloning must be done because the quantity of DNA required is usually more than can be practically collected from blood samples, and also because individual dairy cattle are not maintained permanently in the herd. This cloning allows for a permanent source of mitochondrial DNA from each animal. Cloning involves segmenting the mitochondrial DNA by using restriction endonucleases and then ligating enzymatically this segment to a vector by commonly used methods such as those described by Hackett, et al., P. B., Fuchs, J. A., and Messing, J. W. (*An Introduction to Recombinant DNA Techniques*, (Benjamin/Cummings Publishing Co., 2nd Ed. 1988). The recombinant constructs then are introduced into the Escherichia coli cells for propagation and amplification of the recombinant plasmid. This will yield an amount of the targeted mitochondrial DNA sufficient for restriction fragment length polymorphism analysis.

Another method used in one laboratory for amplification of mitochondrial DNA is by the polymerase chain reaction (PCR). We have isolated, amplified by the PCR, and then determined the nucleotide sequence of the PCR-amplified mitochondrial DNA. Even though this procedure allows one to obtain nucleotide sequence data, only the previously described cloning procedure allows one to permanently store the mitochondrial DNA from test animals.

Following cloning, or using directly isolated mitochondrial DNA, the mitochondrial DNA then is fragmented. One method by which this may occur is by digesting the mitochondrial DNA with selected restriction enzymes. A number of different kind of enzymes are employed to obtain an adequate screening. These enzymes will fragment the DNA at particular selected sites, thereby resulting in fragments of known components. The restriction endonucleases are chosen to cause multiple cleavages within the target DNA and to create an optimal population of differently sized cleavage fragments capable of being resolved by gel electrophoresis. The number of restriction endonucleases employed will vary depending upon the size of the population to be screened and, in the example, below reflects the use of at least 10 restriction endonucleases. Restriction digests are conducted according to the specification of the supplier. The use of restriction endonucleases to measure mitochondrial DNA sequence relatedness is known and has been discussed, for example, by Avise, J. C., Lansman, R. A., and Shade, R.0., "The Use of Restriction Endonucleases to Measure Mitochondrial DNA Sequence Relatedness to Natural Populations", Genetics 92: 279 (1979). Examples of restriction endonucleases that are useful in characterizing bovine mitochondria are listed below. These are only examples; other endonucleases can be used. In general, these will produce between 5 and 25 fragments that are larger than 100 base pairs. See. e.g., Anderson, S., deBruyjn, M. H., Coulson, A. R., Eperon, I. C., Sanger, F. and Young, I. G., J. Mol. Biol., 156:683 (1982). Although by using 20 different enzymes, a screen could be extended to cover about 220 recognition sites, far less extensive screens such as those discussed below in the example may be employed with satisfactory results.

TABLE 1

| Restriction Endonucleases | | | | | | | |
|---|---|---|---|---|---|---|---|
| AccI | (10)* | FokI | (21) | Sau96 | (12) | StuI | (9) |
| AhaIII | (11) | HaeIII | (29) | ScaI | (9) | StyI | (10) |
| BanII | (12) | HincII | (10) | ScrF1 | (14) | TaqI | (21) |
| BbvI | (10) | HpaII | (16) | SfaN1 | (21) | Tth111 | (24) |
| BsmI | (10) | HphI | (19) | SpeI | (8) | XbaI | (6) |
| EcoRII | (9) | Sau3A | (19) | SspI | (14) | ShoI | (5) |

TABLE 1-continued

Restriction Endonucleases

Fnu4H1 (15)

*The number in parenthesis is the number of expected fragments from the complete mtDNA that will be larger than 100 base pairs.

Fragments resulting from digestion with restriction endonucleases are then subjected to agarose gel electrophoresis. This process is widely known to those skilled in molecular biology. Briefly, the fragments are first end-labeled with radioactive nucleotides and then are placed in a gel of a substance which provides a homogenous matrix, for example, agarose or polyacrylamide. The gel is permeated with a buffered aqueous solution, and the fragments move in an electrical field towards the positive pole, depending on their net charge. This analysis will reveal nucleotide sequence heterogenity at random sites throughout the bovine mitochondrial DNA. This is useful in analysis of the mitochondrial DNA.

Any observed polymorphism can be verified by sequencing the nucleotides involved in the polymorphism and observing sequence heterogeneity. Sequencing nucleotides of DNA can be performed by the dideoxy method described by Sanger, et al. 1977. [Spanger, F., S. Nicklen, and A. R. Coulson. "DNA Sequencing With Chain-Terminating Inhibitors", Proc. Natl. Sci. USA. 74:5463 (1977)]. The presence or absence of a polymorphism then is compared with the phenotypic expression of a trait. Obviously, there are many methods for associating a particular trait with the sequenced DNA. The concept is to compare the maternal lines that contain or do not contain the particular genetic marker. If, for example, of 38 cow lines analyzed, 28 have the marker and the rest do not, one would then attempt to associate a particular trait with the presence or absence of that marker. This is then confirmed by looking at the phenotypic expression of the various lines.

An animal model, which is a mixed linear model, is used to estimate the effects due to maternal lineages. Effects are classified as either fixed (repeatable) or random (not repeatable) and are simultaneously estimated. The fixed effects have properties of Best Linear Unbiased Estimates, and the random effects are Best Linear Unbiased Predictions. In this case maternal lineages have been classified as fixed when lineages were determined by tracing cows to their origin in the *Holstein, Friesian Herdbook* of America, and also classified molecular polymorphism or sequences as fixed.

DESCRIPTION OF EXPERIMENTAL ANIMALS

Cows in this study were from a selection experiment founded at Iowa State University in 1968. Heifers for this herd were purchased form 38 Holstein breeders throughout Iowa to keep the herd as genetically broadbased as possible. Cows were bred artificially to sires from commercial artificial insemination organizations, allowing a continuous influx of nuclear genes. Frequencies of bovine lymphocyte antigen phenotypes were similar to frequencies in the U.S. Holstein population, meaning that these nuclear genes are likely representative of the entire U.S. Holstein population. Females were assigned to groups and artificially mated to bulls with either high or average estimated additive genetic transmitting ability for milk yield. Females born in each group were mated to new bulls chosen for that group, thus forming divergent selection lines that differed by 1308 kg of milk per cow per lactation when these data were analyzed.

Ancestral pedigrees of registered foundation females in the herd were tracked backward through the Holstein-Friesian Herd Book. Eighty-one distinct maternal lineages were defined by convergence of maternal pedigrees after 1885. It is possible that these lineages would have been found to converge to fewer lineages had registration records been kept prior to importation of these cows from Europe in about 1885.

Thirty-six maternal lineages had surviving members in the herd when samples for nucleotide sequencing were collected. These lineages had from one to six purchased foundation females in the herd. Nucleotide sequence polymorphism data were obtained and all cows within the same maternal lineage that were ever in the herd were assumed to have identical mtDNA. Because of the among-lineage emphasis of the comparisons in the clonal nature of propagation of mitochondrial DNA, each lineage was represented by at least two cows.

Isolation of Mitochondrial DNA

Total leukocytes were isolated from 400 ml of anticoagulated blood, obtained by jugular venipuncture, by low-speed centrifugation after erythrocyte lysis with 140 mM ammonium chloride, pH 7.4. Leukocytes were lysed with 1% wt/vol Triton X-100 in the presence of 1% wt/vol sodium dodecyl sulfate. Nuclei and cell membranes were separated by the cytosolic fraction by centrifugation at 12,000×g for 5 min. Soluble proteins were extracted from the resulting supernatant with 1:1 phenol:chloroform, and nucleic acids were precipitated from the aqueous phase with 3 vol. ethanol. This procedure yielded a mixture of supercoiled and relaxed covalently closed and nicked circular mitochondrial DNA molecules, RNA and only trace amounts of nuclear DNA contaminants (Koehler et al., 1988 as cited earlier).

Selection and Cloning

The region of the mitochondrial DNA molecule that includes the D-loop, which is markedly variable across mammalian species and in which mutations had been detected previously in Holstein cattle, was chosen as the target of the screen. The segment of the mitochondrial DNA molecule from the PstI restriction endonuclease cleavage site at nucleotide (nt) 15,738 to the SstI cleavage site at nt 3,684 was excised and ligated enzymatically into the multiple cloning site of the 3.2 kilobase phagemid cloning vector pUC118. This segment constituted one fourth of the mitochondrial DNA molecule. The recombinant insert DNA was 4,284 base pairs (bp) long and included a 52-bp tRNA$^{Pro}$ gene, the 910-bp D-loop region, the 66-bp$^{Pro}$ gene, the 954-bp 12S rRNA gene, the 66-bp tRNA$^{Val}$ gene, the 1,570-bp 16S rRNA gene, the 74-bp tRNA$^{Leu}$ gene and a 592-bp portion of the first mitochondrially coded subunit of the nicotinamide adenine dinucleotide dehydrogenase complex (ND 1 gene).

Recombinant constructs were introduced into Escherichia coli TG-1 cells (K12; hsdD5, supE, thi, [lac-pro]/f':traD36, proA+B+, lacI$^q$, lacZ M15) by the calcium-heat shock method (Mandel, M. J. and Higa, A., "Calcium Dependent Bacteriophage DNA Infection," *J. Mol. Biol.*, 53:154 (1970)). Transformation was confirmed by insertional inactivation of vector alpha complementation of isopropyl-B-D-thiogalactopyranoside-induced B-galactosidase activity in ampicillin-resistant colonies. Amplified recombinant plasmids were isolated from 50-ml Luria broth cultures of transformed bacteria by alkaline lysis (Birnboim, H. C. and Doly, J., "A Rapid Alkaline Extraction Procedure for Screening Recombinant Plasmid DNA", Nucleic Acids Res., 7:1513 (1979)) to yield an amount of the target mitochondrial DNA sufficient for restriction fragment length polymorphism (RFLP) analyses.

EXAMPLE OF ESTIMATION OF MATERNAL LINEAGE EFFECTS

Cows in our reseach herd were traced by maternal lineages to foundation femals in the Holstein-Friesian Herdbook to establish maternal lineages. Solution for maternal lineages were obtained from the following animal model.

$$Y_{ijklmno} = \mu + YS_i + P_j + ML_k + Ll + G(L)_{m:l} + PE_n + A_n + e_{ijklmno}$$

Effects in the model are as previously defined except $L_l$ is the "high" or "average" sire selection line; $G(L)_{m:l}$ is the mth sire birthyear group nested in the lth selection line; $PE_n$ is the permanent environmental effect of the nth animal with a record; and $A_n$ is composed of breeding values of sire and dam and a segregation effect and is the additive genetic effect of the nth animal.

Because animal models are usually large, conventional tests of significance, requiring elements of variance-covariance matrices and, hence, direct inversion, are often not feasible. A test of significance using mixed model conjugate normal equations was developed to test significance of maternal lineage effects. Variance ratios for random effects in the model were calculated from results of our variance component estimation. Maternal lineages were evaluated as fixed effects in this animal model including random animal and permanent environment effects. Ranges of maternal lineage estimates were 2934 kg milk, 154 kg fat, and 0.907 percent fat. (Table 1) Maternal lineages significantly affected kg fat and fat percentage. (Table 3) Maternal lineages also affected calculated net energy of milk, but were not apparently important for solids-not-fat yield or concentration. (not shown in Tables)

TABLE 2

Ranges of estimates or solutions of maternal lineage effects from animal model analysis

| Trait | Maternal Lineage Range | $\sigma_p^1$ |
|---|---|---|
| MEMILK[2] | 2934 | 1514 |
| MEFAT[3] | 154 | 59 |
| FAT %[4] | .907 | .393 |

[1]With herd phenotypic standard deviation.
[2]Mature equivalent, 305-day milk yield.
[3]Mature equivalent, 305-day milk fat yield.
[4]Milk fat percentage.

TABLE 3

|  | Trait[1] | F | P > F |
|---|---|---|---|
| Fixed | MEMILK | 1.17 | .188 |
| sire | MEFAT | 1.47 | .017 |
| groups | FAT % | 1.71 | .001 |
| Westell | MEMILK | 1.09 | .308 |
| groups | MEFAT | 1.39 | .035 |

TABLE 3-continued

| Trait[1] | F | P > F |
|---|---|---|
| FAT % | 1.82 | .001 |

[1]For abbreviations, see Table 2.

EXAMPLES OF RELATING MOLECULAR EVIDENCE TO TRAITS OF ECONOMIC IMPORTANCE

Table 4 has location, type, and frequency of the 17 most common sequence polymorphisms of the mtDNA D-loop in this herd of Holstein dairy cattle. Only those polymorphisms occurring in at least 4 percent of cows in the herd are listed, because information on markers occurring in a very small number of cows would not be statistically informative. Transitions at bp 169 and 216 occurred in 80 and 84 percent of cattle, respectively. The probable explanation is that the cow originally sequenced, Anderson, S., M. H. L. deBruijn, A. R. Coulson, I. C. Eperow, F. Sanger, and I. G. Young 1982, Complete sequence of bovine mitochondrial DNA. J. Mol. Biol. 156:683, had the rarer genotype at those two sites. From 30 to 608 cows were polymorphic at individual bp sites of the least and most frequent mtDNA D-loop sequence difference, respectively.

Production records of all cows in the 36 maternal lineages with known mtDNA D-loop sequences were considered. Milk and fat yield records adjusted to a uniform age and lactation length, or mature equivalent (ME), basis were obtained. Percentages in milk of fat and solids-not-fat (SNF) which is total solids in milk less fat in milk, were known for each record of each cow. Up to seven production records were used for individual cows.

Because mitochondria play an extensive role in energy metabolism, mtDNA polymorphism may alter energy content in milk. Fat, protein, and lactose are the carriers of energy in milk; however, information was complete since 1968 only for fat and solids-not-fat, which combines protein, lactose, and minerals. Net energy concentration in milk, which is based on fat and SNF, was calculated in terms of kilocalories per kilogram of milk and multiplied by lactation milk yield to approximate lactation energy production in terms of megacalories.

To evaluate the effect of mtDNA D-loop sequence polymorphism, each cow was assigned a value of 1 if polymorphic or 0 if not polymorphic with respect to the first published mtDNA sequence at each of the 17 locations considered. Each production trait was analyzed individually with the following animal model:

$$Y_{ijknp} = \mu + YS_i + P_j + X_k + \beta_1 + \ldots + \beta_{17} + PE_n + a_n + e_p,$$

where $Y_{ijknp}$ is the milk, fat, fat percentage, SNF, SNF percentage, energy concentration, or lactation energy record; $\mu$ is an overall mean; $YS_i$ is the effect common to all cows calving in year-season; $X_k$ is the effect common to cows in either the high or average selection line; $\beta_1$ to $\beta_{17}$ are the binomial regressions of production record on mtDNA D-loop sequence polymorphisms; $PE_n$ is permanent environmental effect common to all records of cow n; $a_n$ is effect of animal n and is composed of the additive genetic contribution of sire and dam breeding values and a Mendelian sampling effect; and $e_p$ is a random residual.

Regression of production traits on mtDNA D-loop polymorphism was of primary interest. Effects of the overall mean, year-season of calving, parity, and selection line were treated as fixed effects in the mixed model to account for explainable environmental background. Additive genetic covariances among related individuals were incorporated in this model. Permanent environment and additive genetic effects were treated as random and have properties of Best Linear Unbiased Prediction (BLUP). Random effects were assumed to be normally and independently distributed with mean expectations of zero. Variance among permanent environments was assumed to be var(PE)=1 $\sigma_{PE}^2/\sigma_e^2$, where 1 is an identity matrix and $\sigma^2$ is error variance. Variance among animals was assumed to be var(a)=A $\sigma_a^2/\sigma_e^2$, where A is the numerator relationship matrix, Henderson, C. R. 1984. Applications of linear models in animal breeding. University of Guelph, Guelph, Canada. A included sires and dams of all cows back to foundation cows and included information for sires and paternal grandsires of bulls with daughters in the herd. Regression coefficients for sequence polymorphism are Best Linear Unbiased Estimates and were obtained by iterative methods described elsewhere, M. M. Schutz, A. C. Freeman, D. C. Beitz, and J. E. Mayfield, *J. Dairy Sci.* (In Press) (1992), incorporated herein by reference.

A total of 1800 records of 728 cows were used in this study. Along with effects of 17 mtDNA locations, there were 33 year-season, 7 parity, 2 selection line, 728 permanent environment, and 950 animal effects. Animal, or additive genetic, effects were for 728 cows with records, 197 relatives without records, and 25 phantom parent groups to account for genetic similarities among animals without relationship or production information.

Table 5 has overall means of production traits along with their regressions on nucleotide sequence differences. The polymorphism at base pair (bp) 363 has previously been associated with milk and fat yield and fat percentage. This site has since been shown to be highly heterogeneous within maternal lineages, and is therefore unstable for use as a marker. Regressions of production on the polymorphism at bp 363 will not be reported because the sequence difference can not be assumed uniform within maternal lineages.

Eleven nucleotide sequence polymorphisms significantly influenced at least one production trait and traits were influenced in both positive and negative directions. A single Adenine to Guanine transition at bp 169 related to increased production of 482 kg of milk, 24 kg of fat, 51 kg of SNF, and 456 megacalories of energy per cow per lactation. On a purely evolutionary basis, site 169 previously has been found to demarcate two distinct mitochondrial families of cattle in the Holstein population, Lindberg, G. L. 1989. Sequence heterogenity of bovine mitochondrial DNA. Ph.D. Dissertation. Iowa State Univ. Libr. Ames University Microfilm No. DA-9014925 Ann Arbor, Mich.

Polymorphism at site 16074 had a large positive effect on milk, fat, and SNF yield and lactation energy, while polymorphism at site 16231 had a negative effect on the same traits. Fat percentage in milk and energy concentration of milk were significantly affected in cows with polymorphism at sites 16058, 16085, 16230, and 16247. Effects of polymorphism on SNF percentage were small. Possibly, larger effects would have been observed for lactose and protein if data for those components were individually available. Effects as large as these found are certainly economically important.

An overall test of significance was used to determine whether effects of D-loop polymorphisms were specific for individual locations. That the effect of a D-loop sequence polymorphism being present differs among bp sites was tested versus the null hypothesis that the effect of the presence of a polymorphism at one site equals the effect at any other site. Effects of presence of D-loop polymorphism at different sites were significant for milk fat yield (P>F<.06).

Reproductive and health traits also have economic importance in dairy cattle improvement programs. Table 6 has regressions of reproduction and health costs on sequence polymorphisms in the mtDNA D-loop. Number of days open and number of breedings (artificial inseminations), along with reproductive costs, were the measures of reproduction considered. Reproductive costs included costs of insemination and semen, as well as costs of reproductive exams and treatments for postcalving disorders such as metritis and retained placenta.

In addition to reproductive costs, health differences were measured by mammary costs and total health costs. Using costs of health disorders was necessary because incidences of specific events or diseases occur too infrequently to be of use in analysis of data from a single herd. Health costs were grouped by body systems and total health cost is the sum of reproductive, digestive, mammary, respiratory, and skin and skeletal costs. Mammary costs reflected costs of treatment and medications required for cows with mastitis or injured teats, but discarded milk value was not included.

Polymorphism at bp 169 was associated with days open, and reproductive costs and days open were increased in animals polymorphic at bp 16058. There was a very large favorable impact on the reproductive complex in cows with mtDNA D-loop sequence difference at bp 16085. This single T to C transition was related to a decrease of 36 days open, one insemination, and $12.82 in reproductive costs. Thirty-six days open is nearly 2 reproductive cycles.

Mammary costs were altered in cows with mtDNA D-loop sequence polymorphisms at four locations. None were locations significantly affecting milk or milk fat yield or fat percentage. Total health costs were increased when polymorphisms at bp 106 and 16074 occurred, and decreased when polymorphisms at bp 216 occurred. Significant effects were not observed for costs of digestive, respiratory, and skin skeletal cost categories. Incidences of health disorders in these systems were sparse.

Current dairy cattle breeding programs are centered around selection of bulls used for artificial insemination. Two-stage selection is practiced for bulls entering artificial insemination organizations. The first stage is pedigree selection, which is based on sire and dam information. Bulls are finally chosen for extensive use based on a progeny test. The largest selection differentials are for the sire to bull pathway where mtDNA polymorphism is not important if the mitochondrial genome is transmitted only from female parents. The dam to bull pathway is equally important, but the accuracy of selection is less than at the sire to bull pathway. A bull's estimated transmitting ability based on pedigree may be biased if the contribution from his dam is not adjusted for mitochondrial influence on her records. While the bull would acquire mtDNA from the dam, it would not be transmitted to his offspring. Adjustment of bull dam's records for mtDNA influences would allow more accurate prediction of expected genetic contribution of a bull to his daughters.

Data from our experimental herd can be used to demonstrate the magnitude of adjustments that could be expected for bull mothers. Over 4½ years we had 41 cows from 19 different lineages that were in the top 2% of cows in the United States, which qualifies them as potential bull mothers. The top 2% was imputed by USDA-AIPL. The range of maternal lineage effects for these cows was positive 76.4 kg to a megative 30.9 kg fat. So, without adjustment for maternal lineage effects these cows as bull mothers would have had 76.4 kg more and 30.9 kg less fat included in their phenotypic estimates. Thus, bull mothers would have been over and under estimated, respectively.

The dam to cow pathway has traditionally been selected least intensely. However, new developments in reproductive technology and embryo manipulation seem poised to make this pathway of selection more viable. Differences in mtDNA could be incorporated into embryo transfer breeding programs to better choose donor and recipient females to produce replacement heifers. Current cloning techniques require nuclear transplantation into an enucleated ovum without regard to cytoplasmic content. Potential exists for using mtDNA sequence polymorphism to identify ova of females with inferior nuclear genetics in superior mtDNA background as candidates for enucleation and a subsequent introduction of nuclei with greater genetic potential.

TABLE 4 location, type, and frequency of seventeen most common sequence polymorphisms of mtDNA D-loops in a herd of dairy cattle

| Location in D-Loop[a] | polymorphic event | Frequency | Location in D-Loop[a] | Polymorphic event | Frequency |
|---|---|---|---|---|---|
| 8 | G-A | .07 | 16058 | C-T | .12 |
| 106 | T-C | .14 | 16074 | T-C | .07 |
| 169 | A-G | .80 | 16085 | T-C | .05 |
| 216 | Var. length G-C run | .84 | 16111 | A-C* | .04 |
|  |  |  | 16113 | T-C | .11 |
| 363 | C-G* | .46 | 16141 | T-C | .11 |
| 16022 | G-A | .14 | 16230 | C-T | .06 |

TABLE 4-continued location, type, and frequency of seventeen most common sequence polymorphisms of mtDNA D-loops in a herd of dairy cattle

| Location in D-Loop[a] | polymorphic event | Frequency | Location in D-Loop[a] | Polymorphic event | Frequency |
|---|---|---|---|---|---|
| 16049 | C-T | .08 | 16231 | C-T | .12 |
| 16057 | G-A | .12 | 16247 | C-T | .13 |

[a]Location is defined by the first published mtDNA sequence (Anderson et al., 1982). Polymorphic event and frequency is also with regard to that sequence.
*Base pair substitution is a transversion.

TABLE 5

Regression of production on sequence polymorphisms in the mtDNA D-Loop and overall production means in a herd of dariy cattle

| Location in D-Loop | Milk (kg) | Fat (kg) | SNF (kg) | Lactation Energy (Mcal) | Fat (%) | Snf (%) | Energy Concentration (Kcal/kg) |
|---|---|---|---|---|---|---|---|
| 8 | 235 | 1 | 19 | 85 | −.21 | −.04 | −2 |
| 106 | 464 | 16 | 47 | 343 | −.03 | .08 | 2 |
| 169 | 482* | 24** | 51* | 456* | .05 | .05 | 6 |
| 216 | −157 | 1 | −7 | −10 | .07 | .09+ | 10 |
| 16022 | −113 | 6 | −26 | −162 | .04 | .01 | 3 |
| 16049 | 989+ | 29 | 102+ | 756 | −.07 | .17 | 1 |
| 16057 | −577+ | −21 | −48 | −399 | .01 | .11 | 7 |
| 16058 | 39 | 20 | 9 | 225 | .30* | .06 | 31+ |
| 16074 | 842* | 37** | 85* | 749** | .14 | .05 | 16 |
| 16085 | −197 | −20 | −36 | −343 | −.21+ | −.19+ | −29+ |
| 16111 | 107 | −5 | 15 | 52 | −.05 | .05 | −3 |
| 16113 | 32 | 3 | −10 | 3 | .09 | −.21+ | −3 |
| 16141 | −336 | −8 | −35 | −198 | .10 | −.05 | 6 |
| 16230 | 383 | 33 | 39 | 490 | .39** | .06 | 39* |
| 16231 | −650+ | −28 | −61+ | −522+ | −.12 | −.01 | −12 |
| 16247 | 351 | 21 | 32 | 346 | .17* | −.01 | 16+ |
| Overall Mean[a] | 8085 (1771) | 288 (60) | 745 (165) | 5888 (1225) | 3.63 (.44) | 9.21 (.40) | 732 (50) |

[a]Overall standard deviations are in parentheses.
**P > t ≤ .01.
*P > t ≤ .05
+P > t ≤ .10.

TABLE 6

Regression of reproduction and health costs on sequence polymorphisms in the mtDNA D-Loop and overall means of reproduction and health cost means in a herd of dairy cattle

| Location in D-Loop | Days open (d) | Number of Breedings (n) | Reproduction Costs ($) | Mammry Costs ($) | Total Health Costs ($) |
|---|---|---|---|---|---|
| 8 | −31.7 | −.73 | −6.12 | 24.79+ | 10.22 |
| 106 | 0.5 | .13 | −2.66 | 16.24+ | 21.28+ |
| 169 | 14.6+ | .34 | 6.05+ | .84 | 11.47 |
| 216 | −0.5 | .12 | .07 | −9.70+ | −14.54+ |
| 16022 | −13.4 | −.12 | −3.89 | 9.77 | 1.83 |
| 16049 | 16.1 | .28 | .88 | 4.58 | 17.94 |
| 16057 | 9.7 | .14 | −2.90 | −9.31 | −15.93 |
| 16058 | 28.3+ | .68 | 2.44 | 2.94 | 18.44 |
| 16074 | 3.7 | .34 | 6.28 | 13.56 | 25.93+ |
| 16085 | −36.3* | −.99* | −12.82+ | −2.31 | 19.70 |
| 16111 | −14.1 | −.64 | −4.06 | −8.94 | −11.19 |
| 16113 | −5.5 | −.63 | −1.64 | 1.18 | −2.24 |
| 16141 | −11.7 | −.36 | −3.01 | −15.67+ | −19.58 |
| 16230 | −4.4 | −.02 | −2.04 | 13.10 | 12.12 |
| 16231 | −16.0 | −.53 | −3.53 | −4.81 | −11.30 |
| 16247 | −8.2 | .02 | 2.47 | 3.19 | 7.71 |
| Overall mean[a] | 135 (72) | 2.61 (2.24) | 38.73 (34.49) | 19.07 (43.8) | 77.67 (60.14) |

[a]Overall standard deviations are in paranthases.
*p > t ≤ .05.
+p > t ≤ .10.

Mitochondrial DNA (mtDNA) displacement-loop (D-Loop sequence polymorphism information from 36 maternal lineages was evaluated. Of 17 base pair substitutions evaluated, several were significantly associated with milk, fat, and solids-not-fat-production. Another marked a large impact on fat percentage and net energy concentration. Positive and negative effects on all production traits were observed. One base pair substitution was related to a large favorable decrease in days open, number of breedings, and reproductive costs.

Maternal lineage groups defined by several methods of classification using mtDNA sequence characteristics were evaluated with animal models. Groups defined as those maternal lineages with or without base pair substitution at nucleotide 169 accounted for increased milk fat and estimated milk energy production. Clustering the 36 maternal lineages using 17 mtDNA D-loop sequence differences produced groups with significant effect on fat percentage and energy concentration.

This method allows one to employ analysis of the mitochondrial DNA to predict which animals differ in traits of economic importance. Thus, for example a single Adenine to Guanine transition at bp 169 relates to increased milk production as measured by volume and lowered milk fat; polymorphism at 16074 has a large positive effect on milk, fat and SNF; polymorphism at bp 16058 is evidence of increased days open and reproductive costs. This provides a new source of genetic material to use in evaluating inheritance in an animal. Mitochondrial influences on a dam's production are not transmitted through her male offspring to his progeny, and such cytoplasmic effects currently are included in an estimate of the dam's transmitting ability, which may cause the dam's transmitting ability to be over- or under-estimated for the purpose of predicting her son's progeny test. Knowledge of the dam's maternal effect allows adjusting her transmitting ability to accurately predict her son's progeny test. This method provides a basis for exploitation of potential gains from selection from more efficient maternal genotypes based upon cytoplasmic differences. It is also possible to identify cows with good maternal traits as herd replacements. Even small differences in feed efficiency can be exploited and would have major economic importance when applied to the dairy cattle population. By way of another example, feed costs are 40 to 50% of dairy production expenses, and even if only a 5% increase in feed efficiency resulted from application of mitochondrial DNA to selective practices, a savings of over 3 billion dollars annually could be realized by the dairy industry in the United States.

Other potential applications include the possibility of combining and transplanting superior mitochondrial DNA with superior nucleic DNA, resulting in animals which predictably will carry an inheritable desired trait, such as high milk production.

Another application is choice of cows from the best maternal lineages (cytoplasmically or mitochondrically based), as donors for embryo transplants. The practice of embryo transplantation is used extensively in the dairy industry.

Thus, it is apparent that the invention accomplishes at least all of its objectives.

What is claimed is:

1. A method of evaluating the material mitochondrial phenotypic contribution to economic traits of milk production and reproduction efficiency of a dairy cow comprising:
    assaying for the presence of one or more genetic markers in the mitochondrial D-loop of said cow.
2. The method of claim 1 wherein said genetic mitochondrial marker is selected from the group consisting essentially of: a mutation event at D-loop position 8, 106, 169, 216, 363, 16022, 10649, 16057, 16058, 16074, 16085, 16111, 16113, 16141, 16230, 16231, or 16247.
3. The method of claim 1 wherein said milk production traits include total output of milk, fat content of milk, solids-not-fat content of milk, and energy concentration in milk.
4. The method of claim 1 wherein said reproduction efficiency includes number of days open and number of breedings.
5. The method of claim 1 wherein the genetic D-Loop mitochondrial marker comprises the presence of one or more polymorphisms, said polymorphisms selected from the group consisting essentially of: an adenine at position 8, a cytosine at position 106, a guanine at position 169, a guanine at position 363, an adenine at position 16022, a thymine at position 16049, an adenine at position 16057, a thymine at position 16058, a cytosine at position 16074, a cytosine at position 16085, a cytosine at position 16111, a cytosine at position 16113, a cytosine at position 16141, a thymine at position 16230, a thymine at position 16231, and a thymine at position 16247.
6. The method of claim 1 wherein said marker is a guanine at position 169 and is indicative of increased milk production.
7. The method of claim 1 wherein said marker is a cytosine at position 16074 and is indicative of decreased milk production, solids-non-fat yield, and lactation energy and lowered fat content.
8. The method of claim 1 wherein said marker is a thymine at position 16231 and is indicative of decreased milk fat content, solids-non-fat yield, and lactation energy.
9. The method of claim 1 wherein said marker is selected from the group consisting of: a thymine at position 16058, an adenine at position 16085, a thymine at position 16230, and a thymine at position at 16247 and is indicative of increased fat percentage and energy concentration of milk.
10. The method of claim 1 wherein said marker is a cytosine at position 106 or position 16074 and is indicative of increased total health costs.
11. The method of claim 1 wherein said marker is a guanine at position 169 is indicative of increased days open.
12. The method of claim 1 wherein a cytosine at position 16085 is indicative of increased days open (days between calving and conception) and number of breedings to achieve conception.
13. Genetic mitochondrial D-Loop markers for milk production and reproductive efficiency traits in dairy cattle, said markers comprising the group consisting essentially of: a transition at mitochondrial D-loop position 8, 106, 169, 16022, 16049, 16057, 16058, 16074, 16085, 16113, 16141, 16230, 16231, 16247, 363 or 16111.
14. The markers of claim 13 wherein said marker is associated with fat content of milk, solids-non-fat content of milk, total milk production, lactation energy, number of days open, number of breedings.
15. The markers of claim 13 wherein said markers occur in at least 4%.
16. A method of evaluating inheritable milk production and reproduction efficiency traits in dairy cattle by partitioning effects of mitochondrial lineages from nuclear effects, said method comprising:
    isolating mitochondrial DNA from a group of said dairy cows, fragmenting and sequencing said mitochondrial DNA, comparing said mitochondrial DNA of said group of dairy cows to known mitochondrial sequences to detect nucleotide sequence polymorphism, determining the presence of said polymorphic mitochondrial DNA sequences with a milk production phenotypic trait of said dairy cow, and selecting said cattle for favorable breeding features.

* * * * *

UNITED STATES PATENT AND TRADEMARK OFFICE
CERTIFICATE OF CORRECTION

PATENT NO. : 5,292,639

DATED : March 8, 1994

INVENTOR(S) : Beitz et al.

It is certified that error appears in the above-identified patent and that said Letters Patent is hereby corrected as shown below:

Column 13 line 61, cancel "material" and substitute

--maternal--.

Signed and Sealed this

Nineteenth Day of July, 1994

Attest:

BRUCE LEHMAN

*Attesting Officer*  *Commissioner of Patents and Trademarks*